(12) United States Patent
Chandler et al.

(10) Patent No.: US 7,102,665 B1
(45) Date of Patent: Sep. 5, 2006

(54) VEHICLE UNDERBODY IMAGING SYSTEM

(75) Inventors: Scott Chandler, Panama City Beach, FL (US); Chris Doyle, Panama City Beach, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 744 days.

(21) Appl. No.: 10/314,563

(22) Filed: Dec. 10, 2002

(51) Int. Cl.
*H04N 7/18* (2006.01)
*G06K 9/00* (2006.01)

(52) U.S. Cl. ..................................... 348/148; 382/104
(58) Field of Classification Search ........ 348/143–144, 348/148, 151, 159, 156; 382/104; 362/559; 378/57, 88; 701/29
See application file for complete search history.

(56) References Cited

U.S. PATENT DOCUMENTS

| | | | |
|---|---|---|---|
| 5,764,683 A * | 6/1998 | Swift et al. ................... 378/57 |
| 6,052,631 A * | 4/2000 | Busch et al. ................... 701/29 |
| 6,249,567 B1 * | 6/2001 | Rothschild et al. ............ 378/88 |
| 6,856,344 B1 * | 2/2005 | Franz ......................... 348/143 |
| 2003/0193818 A1 * | 10/2003 | Grothe et al. ............... 362/559 |

* cited by examiner

*Primary Examiner*—Gims Philippe
(74) *Attorney, Agent, or Firm*—James T. Shepherd

(57) ABSTRACT

A system and method for imaging underbodies of moving vehicles have a stationary source of radiation to radiate energy upwardly on underbodies of moving vehicles. A stationary video camera adjacent the radiation source on a roadway has an upwardly facing field of view for creating image signals representative of sequential portions of each underbody as each moving vehicle passes overhead. A control station activates the camera and radiation source to create the image signals and creates mosaic signals of all of each underbody from the image signals. A display screen provides a mosaic image of each underbody from its mosaic signals. A virtually real-time inspection or a comparison can be made with previously taken underbody images of the same moving vehicle or with vehicle manufacturers' data for the same vehicular models. Moving cars, trucks, marine vessels, aircraft, can be quickly imaged for inspection and/or comparison by fewer security personnel.

31 Claims, 3 Drawing Sheets

VEHICLE UNDERBODY IMAGING SYSTEM

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

This invention relates to devices and methods for imaging a moving vehicle. More particularly, the imaging device and method of this invention provides mosaic images of the undersides of moving vehicles on a roadway.

Presently, vehicles entering a secure area are randomly selected for inspection. During the inspection, a designated vehicle is stopped, a mirror is rolled beneath the underside, and security personnel make visual inspections. This procedure usually requires several inspectors, is time consuming, and may not enable a full view of all portions of the underbody. At best, this hit-or-miss procedure has questionable value, and, as fiscal and personnel resources become even more strained, the effectiveness of this course of action is further compromised.

Thus, in accordance with this inventive concept, a need has been recognized in the state of the art for a system that provides security personnel a mosaic image of the entire underside of each moving vehicle entering a secure area or going past an inspection checkpoint.

OBJECTS AND SUMMARY OF THE INVENTION

An object of the invention is to provide a method and system for imaging the underbodies of vehicles.

Another object is to provide a method and system for uninterrupted imaging and inspection of the underbodies of all vehicles traveling on a roadway, marine passageway, or taxiway without stopping the vehicles.

Another object is to provide a method and system for imaging the underbodies of moving vehicles and storing the mosaic images of the underbodies for future reference.

Another object is to provide a method and system for imaging moving vehicles and storing mosaic images of the underbodies for comparison or cross-referencing to vehicle manufacturers' data of the same vehicular models or images of the same vehicles taken at an earlier time.

Another object is to provide an imaging system and method that are cost effective by speeding up the imaging-inspection process and increasing the number of inspections while reducing personnel requirements.

Another object is to provide an imaging method and system for mosaicing image portions to build a complete image of a vehicle's underbody with a minimum stationary video cameras.

Another object is to provide a method and system for quickly imaging underbodies of many moving cars, trucks, marine vessels, and/or aircraft traversing a roadway, marine passageway, and taxiway, respectively for inspection and/or comparison by reduced numbers of security personnel.

These and other objects of the invention will become more readily apparent from the ensuing specification when taken in conjunction with the appended claims.

Accordingly, the invention provides a system and method for imaging the underbody of a moving vehicle. A stationary source of radiation radiates energy upwardly onto an underbody of a moving vehicle. A stationary video camera adjacent the radiation source on a roadway has an upwardly facing field of view for creating image signals representative of sequential portions extending the width of the underbody as the moving vehicle passes overhead. A control station activates the camera and radiation source to create the image signals and creates mosaic signals of all of the underbody from the image signals. A graphic display screen provides a mosaic image of the underbody from the mosaic signals. A virtually real-time inspection or a comparison can be made with previously taken underbody images of the same moving vehicle or with vehicle manufacturers' data for the same vehicular model. The underbodies of many moving cars, trucks, marine vessels, aircraft, can be quickly imaged for inspection and/or comparison by reduced numbers of security personnel.

DESCRIPTION OF THE PREFERRED EMBODIMENT

Figure 1:
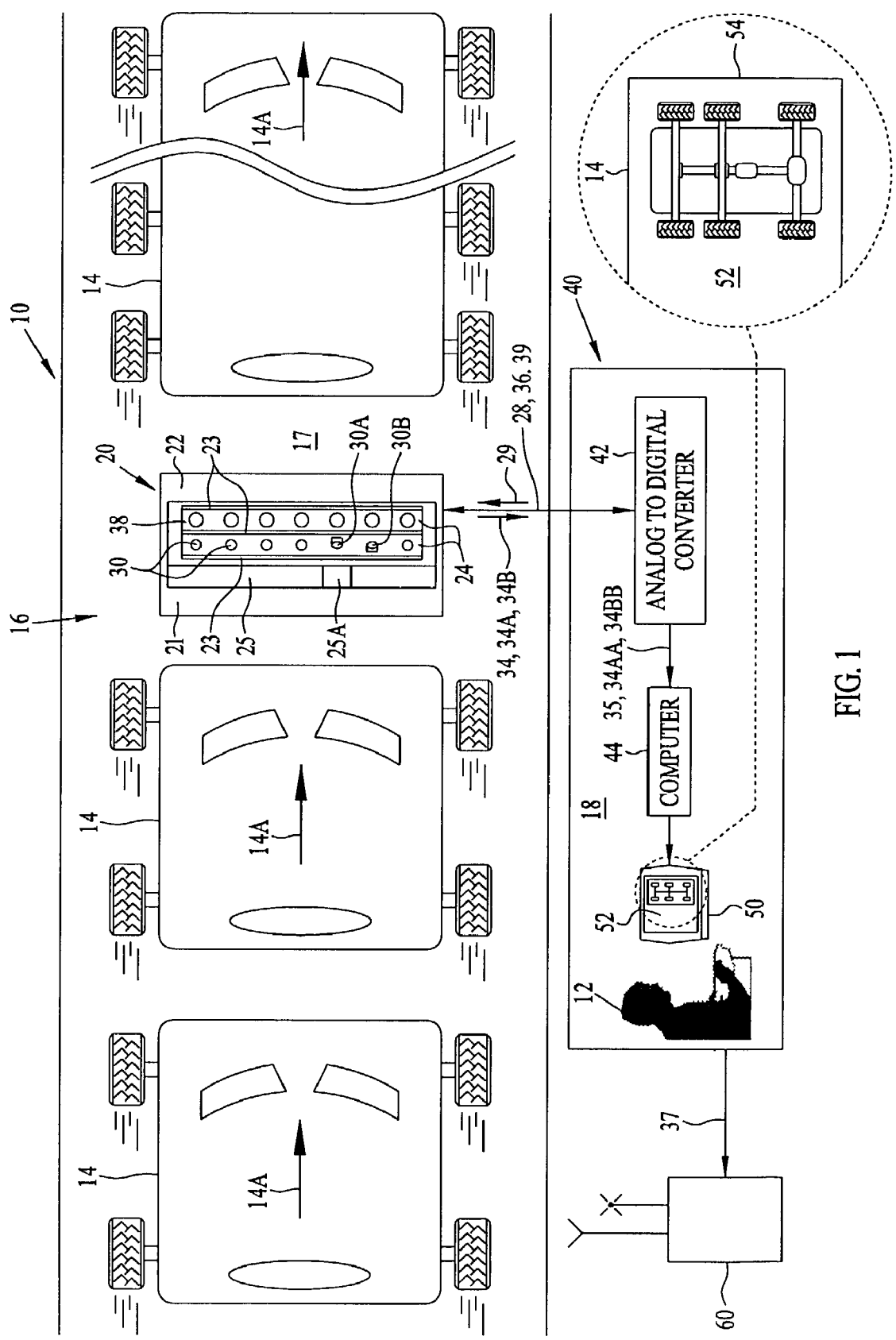
FIG. 1 schematically shows an overhead view of the vehicle underbody imaging system of the invention for imaging the undersides of moving vehicles on a roadway at a control station at a checkpoint.
Figure 2:
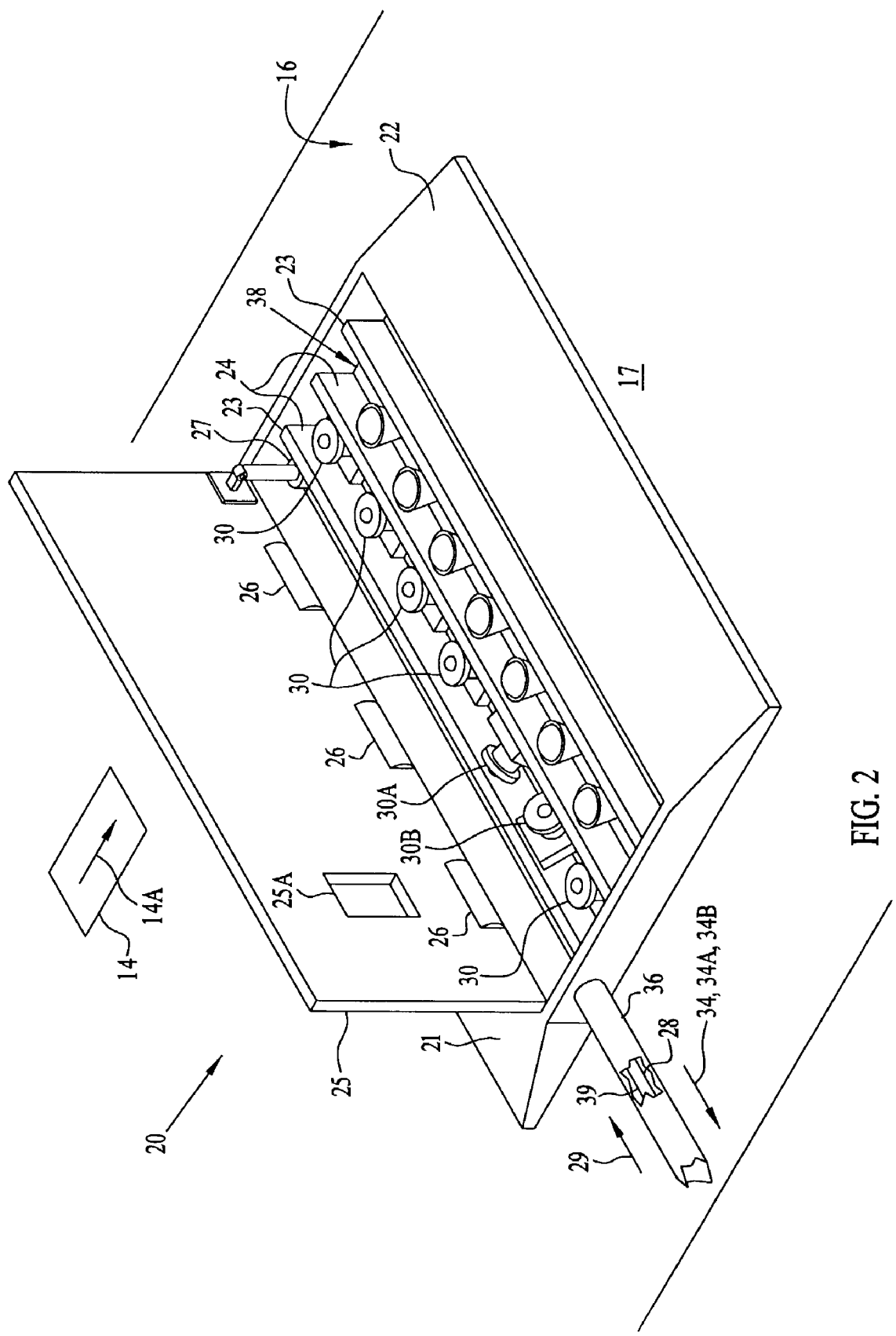
FIG. 2 is a schematic isometric depiction of the housing and its components of the vehicle underbody imaging system on the roadway for taking images of the underside of a vehicle.

Referring to FIGS. 1 and 2, vehicle underbody imaging system 10 of the invention permits security personnel 12 to visually inspect the undersides of vehicles 14 moving in the direction indicated by arrows 14A on their roofs as they travel on a roadway 16 past a checkpoint 18. Checkpoint 18 may be anywhere along roadway 16 or could be at an entrance to a secured area. Imaging system 10 creates a complete mosaic image of the underside, or underbody of each vehicle 14 from partial images. These mosaic images can be gathered from all or selected ones of vehicles 14 on roadway 16.

Vehicle underbody imaging system 10 includes a portable protective housing 20 on roadway 16 that has at least one stationary video camera 30 to provide image signals 34 that are representative of portions of the underbody of each vehicle 14. These image signals 34 are transmitted over a coaxial cable 36 extending from camera 30 to a control station 40 at or remote from checkpoint 18 for observation on a display screen 50. Imaging of each vehicle 14 by stationary camera 30 is done while vehicle 14 is moving between about ten to thirty miles per hour so all vehicles 14 traveling on roadway 16 can be imaged by at least one camera 30; only a few personnel at control station 40 and display screen 50 are needed to monitor the images; and the occupants of the vehicles are not alerted that their vehicles are being imaged.

Protective housing 20 is intended to be placed on the center portion 17 of roadway 16 between the areas where tires of vehicles 14 normally roll. However, since some traffic may wander on roadway 16, protective housing 20 is robustly constructed to withstand anticipated pounding from tires of vehicles 14 that might roll along center portion 17 and onto housing 20. Housing 20 is fabricated from steel and has an up-ramp part 21 on the incoming traffic side and a down-ramp part 22 on the departing traffic side. Several elongate ridges 23 and adjacent elongate channels 24 extend the length of protective housing 20, and an elongate hinged lid 25 covers or exposes elongate channels 24. Elongate hinged lid 25 has a long-lived urethane hinge 26 that permits lid 25 full freedom of movement from the closed, or covering position on channels 24 to the open, or exposing position near channels 24.

Protective housing 20 resembles a widely used portable cable protector that protects cables extending across a street from damage by traffic. Like the portable cable protector, protective housing 20 is man-portable and can be picked up and moved from one roadway 16, or location to another. Appropriate handles and conspicuous end boots (not shown) can be added to make relocation easier and make housing 20 more visible.

Urethane hinge 26 can hold lid 25 in the open position as shown in FIG. 2. Tires from a moving vehicle that strays onto center portion 17 will ride up up-ramp part 21, strike, and rapidly close lid 25 to impact and abut ridges 23 and protect the contents of elongate channels 24. As a moving vehicle moves off of lid 25 and onto off-ramp part 22, the inherent biasing force of hinge 26 rotates lid 25 to the open position once again. Optionally, a rotary mechanism 27 (electric motor or solenoid) can be connected to lid 25 and can have a control conductor 28 extending to control station 40. Appropriate control signals 29 from control station 40 selectively activate motor/solenoid 27 to rotate elongate lid 25 to expose channels 24 or to cover channels 24 as lid contacts ridges 23.

At least one stationary camera 30 is centrally located in one of elongate channels 24 and is not exposed to hazards created by tires of vehicles 14 passing overhead or elongate lid 25 as it is quickly closed shut. Camera 30 is oriented to face upwardly toward the underbody of each vehicle 14 passing overhead on roadway 16. Fish-eye-like, or other wide angle lenses 32 can be mounted on camera 30 to assure field-of-view and focal properties for acceptable video images that extend across the width of each vehicle 14. Stationary camera 30 could be fitted in channel 24 and pointing in a direction other than upward. In this case, a suitable arrangement of lenses could be arranged to assure that the sequential images that are taken are of the underbody taken from below the underbody. Camera 30 creates sequential video images extending across the width that in the aggregate are representative of the entire underbody of each vehicle 14 as it passes overhead. Image signals 34 representative of the sequential video images are connected to control station 40 over coaxial cable 36. Many different models of camera 30 can be selected so long as it creates a National Television System Committee (NTSC) composite-video industry-standard output.

Some inspection applications might require more than one camera 30 to assure, for examples, that the width of vehicle 14 can be positively accommodated to create clear image signals 34 of representative video images, different resolution properties in the video images might be desirable, or different radiations could be sensed by different cameras having different radiation responses. More than one camera 30 can be spaced apart side-by-side in the same elongate channel 24 or in adjacent channels. The plurality of cameras 30 can be appropriately activated, time or frequency division multiplexed, and has image signals 34 fed over cable 36 to control station 40 for creating sufficient video images of the underbody.

One camera 30A can be oriented facing through an opening 25A in lid 25 toward vehicles approaching checkpoint 18 on roadway 16. Camera 30A can take a frontal image 34A of each vehicle 14 that includes its license number, and another camera 30B can be oriented in the opposite direction facing toward vehicles departing checkpoint 18 on roadway 16 to take a rear image 34B of each vehicle 14 that includes its license number. Frontal and rear images 34A, 34B can be used in control station 40 to identify each vehicle 14 for comparison or cross-referencing to vehicle manufacturers' data of the same vehicular models or images of the vehicles taken at an earlier time.

Each camera 30 is stationary in housing 20 and a stationary lighting strip 38 is disposed in an adjacent elongate channel 24 to illuminate the underbody, or underside of each vehicle 14. Lighting strip 38 can be a single elongate light source or series of interconnected bulb-like structures that is activated by a control/power lead 39 that extends to control station 40. Lighting strip 38 illuminates the underside of each vehicle 14 as it passes overhead. Lighting strip 38 can be any of many high intensity light sources in the art and can be activated to be continuously on over a sufficient period while video camera(s) 30 provides sequential video images of the entire underside of each vehicle 14. Lighting strip 38 also can be pulsed like a strobe light to coincide with the activation sequence of camera(s) 30 for the sequential video images.

Each video camera 30 can be selected to produce images of visible energy, such as light, or energy outside of the visible spectrum or in other energy bands imperceptible by a human observer, e.g. but not limited to infrared, ultraviolet, etc. When such cameras or sensors are selected, lighting strip 38 can be a continuous or pulsed source that radiates the energy that the selected camera or sensor is responsive to (visible or imperceptible) and selective images can be generated. Image signals 34 representative of imperceptible radiation can be connected to control station 40. Creating selective images of the underbodies with the imperceptible energies can further increase the effectiveness of vehicle underbody imaging system 10 of the invention.

Control station 40 can be at a convenient, permanent or mobile roadside location where security personnel can monitor images from passing traffic on roadway 16. Appropriate power/control conductors 28 and 39 extend from control station 40 to transmit suitable power/control signals 29, 39A to rotate elongate lid 25 to the open position to expose upward facing stationary camera 30 and to activate lighting strip 38 and camera 30. Control station 40 is connected to coaxial cable 36 that receives sequential analog image signals 34 from camera 30 and couples them to an analog to digital converter 42 that digitizes them into digital video image signals 35. Control station 40 has a standard desktop computer 44 receiving the digitized image signals 35 from analog to digital converter 32.

Computer 44 has mosaicing software to mosaic the sequential digitized image signals 35 of the underside of each vehicle 14 into a single composite, or mosaic image 52 of each entire underside. Such mosaicing procedures are known in the art, and a typical procedure is disclosed in U.S. Pat. No. 6,075,905 by Joshua Randy Harding et al. and assigned to Sarnoff Corporation of Princeton, N.J. Real-time mosaic construction, or putting together of sequential digital image signals 35 of the underside of each moving vehicle 14 into a single mosaic image 52 of the entire underside on display screen 50 can be accomplished by computer 44. One way such construction in computer 44 can be done is by including firmware and mosaicing software of the single board vision system marketed as Part # AVA-PCI under the trademark ARCADIA 1™ by Pyramid Vision Technologies of Sarnoff Vision Corporation, P.O. Box 6957, Princeton, N.J. 08543. The associated software and ARCADIA 1™ PCI can process sequential digital image signals 35 such as those generated by one or more stationary cameras 30 into a single mosaic image 52 of the underbody of each vehicle 14 for display on screen 50 and/or storage in computer 44. This capability permits present or subsequent comparison or cross-referencing to vehicle manufacturers' data of the same vehicular models or previously taken images of the same vehicles that also are stored in memory of computer 44.

Display screen 50 can be an LCD panel and/or projector-and-screen 54 large enough for viewing mosaic images 52 of underbodies. Additional graphic display screens 50 (not shown) can be located at other remote locations to apprise other observers for appropriate action.

In operation, vehicle underbody imaging system 10 of the invention can provide virtually real-times images of complete undersides of moving vehicles 14 on roadway 16. As one vehicle 14 approaches up-ramp 21 of housing 20 at speeds between ten to thirty miles per hour, camera 30A facing the oncoming vehicle 14 is activated to create front image signals 34A and couples them to computer 42 of control station 40 for identification.

As vehicle 14 continues to move forward on roadway 16, it drives over, or passes over housing 20. Control/power signals 39A on lead 39 from control station 40 activate stationary lighting strip 38 to turn it on in coincidence with activation of the imaging sequences of camera(s) 30. At least one upwardly facing stationary video camera 30 in housing 20 is activated to begin taking and sending sequential image signals 34 of analog video of overhead passing vehicle 14 over cable 36 to control station 40. If a single camera and lens 30, 32 can create sequential image signals 34 of acceptable clarity and resolution that span the width of vehicle, only this single camera 30 is used. If, however, a plurality of cameras 30 (and lenses 32) are needed to provide acceptable sequential images, then the plurality of cameras 30 are activated and multiplexed in frequency or time division format to create collective sequential image signals 34 that collectively span the width and sequential portions of the underbody of the moving vehicle. Other camera 30B facing toward vehicles departing down-ramp part 22 take a rear image 34B of each vehicle 14. Analog-to-digital converter 42 digitizes the analog signals of the front and rear images 34A, 34B and collective sequential image signals 34 into representative digital vehicle identifying signals 34AA, 34BB and digital sequential image signals 35 and couples the digital signals to computer 44.

The analog video images from cameras 30 on cable 36 are standard NTSC (standard TV images with approximately 30 frames per second). The incoming digitized sequential image signals 35 from A/D converter 42 are processed in computer 44 with the ARCADIA 1™ PCI and software to build the mosaic image of the entire underside with the digitized image signals 35. In other words, the mosaicing process of the ARCADIA 1™ PCI and software electronically places each digitized frame 35 of the analog image signals 34 together into the mosaic image much like the process of manually putting the pieces of a puzzle together. When the scanned vehicle 14 has passed by housing 20, the analog data stream stops, lighting strip 38 turns off, and control station 40 sends a completed mosaic image 52 of the entire underbody of the scanned vehicle to display screen 50. A copy of the completed image is copied and stored to disk of computer 44 and/or sent to other data collection and evaluation stations of a large security system.

Security personnel 12 at control/processor 40 and display screen 50 at checkpoint 18 can view the entire underbody of the scanned vehicle 14. Computer 44 can compare the completed mosaic image or cross-reference it to vehicle manufacturers' data of the same vehicular models or images of the same vehicle taken at an earlier time and stored in memory of computer 44. Any possible discrepancy can be noted. The entire procedure can be quickly accomplished as the imaged vehicle is moving, and the vehicle's occupants are not alerted.

Vehicle underbody imaging system 10 allows inspection of vehicles' undersides without requiring the vehicles to stop. Copies of mosaic images of vehicles can be stored in hard drives for future reference or cross-referenced to a vehicle manufacturer's database. Vehicle underbody imaging system 10 is cost effective since it speeds up the imaging/inspection process and reduces manpower while increasing the number of inspections.

The constituents of vehicle underbody inspection system 10 are man-portable and can be used where needed. Housing 20, camera(s) 30, lighting strip 38, control station 40, display screen 50 and their interconnecting leads and cables are readily unpacked, interconnected, and deployed by only one or more technicians at one location. When underbody imaging may be more beneficial at another location, vehicle underbody inspection system 10 can be packed, transported, and redeployed at the other location quickly without attracting undue attention.

Housing 20 as described above can be modified in accordance with this inventive concept and still provide sequential underbody images. Another design for housing 20 could be a permanent or recently dug cavity covered by a protective steel grate (not shown) in roadway 16. Although the design of this housing is not portable, camera(s) 30 and lighting strip 38 could be placed and properly oriented in the cavity for taking underbody images through openings in the grate. Camera(s) 30 and lighting strip 38 could be removed from the cavity and relocated to another protected place. For example, lenses or mosaics (bundles) of optical fibers could be made to extend to center 17 of a roadway 16 to create an optical path extending to the cameras located at roadside. The lenses and fibers and/or cameras could be quickly placed in the open or somewhat camouflaged on center 17 of roadway 16 to function until disabled by passing traffic.

Several housings 20 each containing camera(s) 30 and lighting strips 38 could be placed on several adjacent roadways, or lanes of a highway and could be suitably connected to one or more control stations 40 and screens 50. Many or all vehicles 14 could be monitored as they move on the highway. Vehicle underbody imaging systems 10 could be located on different roadways that lead into a city for example. Each of these imaging systems 10 could have a radio transmitter 60 connected by a coaxial cable 37 to its control station 40 associated with camera(s) 30 to transmit the imaged data to one or more remote locations where monitoring, comparisons, and responsive actions are initiated. The imaging systems 10 of the invention could thereby create and store several mosaic images of the complete underbody of the same vehicle (or vehicles) under surveillance as an area is traversed. Comparisons of the stored mosaic images with later developed mosaic images will help assure more responsive actions.

Figure 3:
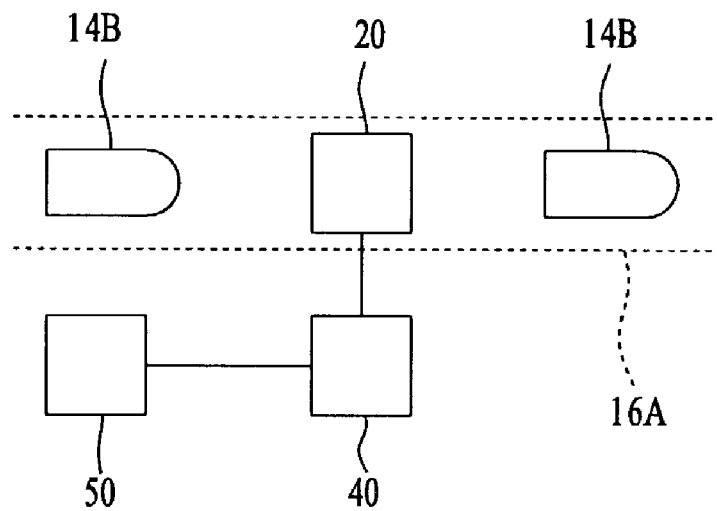
FIG. 3 schematically shows the system of the invention for imaging underbodies, or undersides of ships and boats proceeding along a marine passageway.
Figure 4:
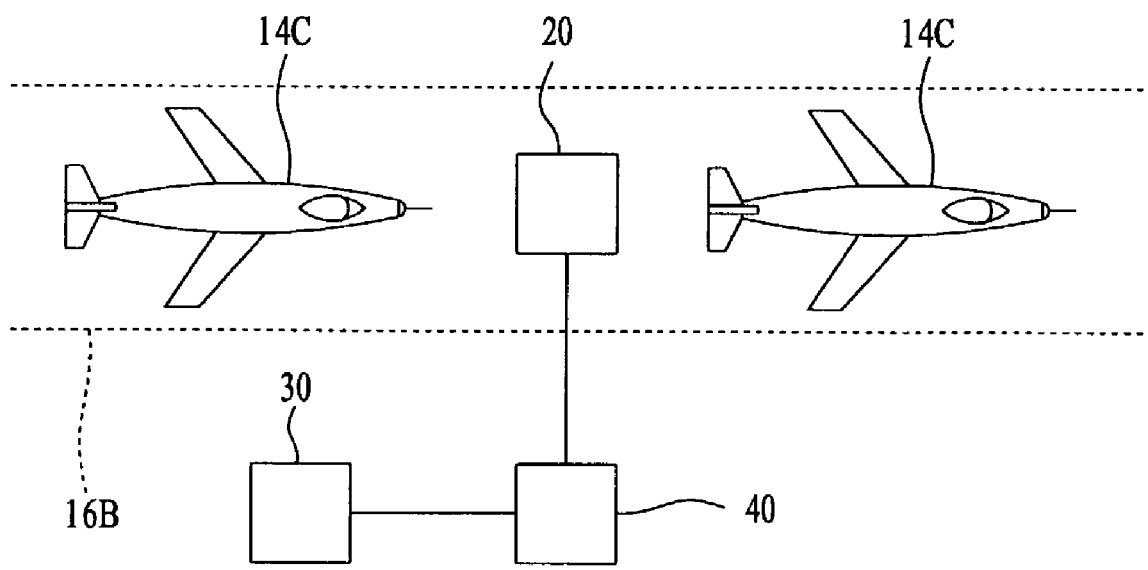
FIG. 4 schematically shows the system of the invention for imaging underbodies, or undersides of aircraft as they proceed along a taxiway.

Referring to FIG. 3, vehicle underbody imaging system 10 of the invention can be used for imaging and inspection of the underbodies, or undersides of hulls of water born vehicles 14B such as boats and ships as they proceed along a waterway or marine passageway 16A. Appropriate measures for water-proofing, pressurizing and locating connections and components referred to above that are contained in housing 20 of imaging system 10 to make them ready for reliable underwater operation beneath the undersides of the hulls can be done by one skilled in the art in accordance with the scope of this invention. Control station 40 and display 50 can be located on nearby land or another vessel and are coupled to the components in housing 20.

Aircraft 14C (air traffic vehicles) can be accommodated on taxiways 16B by imaging system 10. However, consideration must be given to possibly offset housing 20 to avoid damaging camera(s) 30 and strip lighting 38 by aircraft tires mounted on the centerline of aircraft 14C. Station 40 and display 50 are appropriately located near taxiway 16B and are coupled to the components in housing 20. Operation of imaging system 10 for marine and aircraft applications is substantially the same as described above with respect to roadway 16. Visible and imperceptible radiation sources and cameras responsive to these radiations also can be used for marine and aircraft applications.

Having the teachings of this invention in mind, different applications, modifications and alternate embodiments of this invention may be adapted. Vehicle underbody imaging system 10 can be made in larger or smaller sizes or fabricated in different shapes to meet different operational scenarios.

The disclosed components and their arrangements as disclosed herein all contribute to the novel features of this invention. Vehicle underbody imaging system 10 is a portable, cost-effective means to take complete underbody mosaic images without alerting others to reveal the nature of the activity. Therefore, vehicle underbody imaging system 10, as disclosed herein is not to be construed as limiting, but rather, is intended to be demonstrative of this inventive concept.

It should be readily understood that many modifications and variations of the present invention are possible within the purview of the claimed invention. It is to be understood that within the scope of the appended claims the invention may be practiced otherwise than as specifically described.

We claim:

1. A system for imaging the underbody of a moving vehicle comprising:
    a stationary source of radiation adjacent to radiate energy upwardly on an underbody of a moving vehicle;
    a stationary video camera adjacent said stationary radiation source having an upwardly facing field of view for creating image signals representative of sequential portions of said underbody of said moving vehicle passing overhead;
    a control station coupled for activating said camera and radiation source to create said image signals, said control station receiving said image signals from said video camera for creating mosaic signals of said underbody;
    a screen coupled to said control station for displaying a mosaic image of said underbody from said mosaic signals, said control station including a computer activating said radiation source to radiate said energy and said camera to create said image signals, said computer creating said mosaic signals for said screen and storing a copy thereof, and said computer having memory to store earlier mosaic signals of previously taken mosaic images of the underbody of the same vehicle and vehicle manufacturers' data for the same vehicular model for comparison with said copy; and
    a housing having elongate channels between ridges extending the length of said housing and an elongate hinged lid extending the length of said housing to cover said channels and ridges, said housing containing said stationary camera and said radiation source in said channels, said housing being placed on the center portion of a roadway between the areas where tires of vehicles normally roll, and said housing, said hinged lid, and said ridges protecting said stationary camera and said radiation source in said channels from said moving vehicle and other vehicles.

2. The system of claim 1 wherein said stationary camera has a field of view extending the width of said moving vehicle and said image signals are representative of said sequential portions of said underbody extending said width.

3. The system of claim 1 further comprising:
    a plurality of cameras in said channels being disposed to create collective sequential image signals that collectively span the entire width and said sequential portions of said moving vehicle, said computer creating said mosaic signals from said collective image signals.

4. The system of claim 3 wherein said cameras have one camera facing toward approaching traffic to create frontal image signals of said moving vehicle and another camera facing departing traffic to create rear image signals of said moving vehicle.

5. The system of claim 4 wherein said computer receives said frontal image signals and said rear image signals for identifying said moving vehicle.

6. The system of claim 5 wherein said ridges and channels of said housing are adjacent one another and between an up-ramp portion and a down-ramp portion and said hinged lid is rotatable to selectively uncover said channels to expose said cameras and radiation source and cover said channels and abut said ridges to protect said cameras and radiation source.

7. The system of claim 6 further comprising:
    means for rotating said hinged lid to selectively uncover and cover said channels.

8. The system of claim 7 wherein said moving vehicle is part of motor vehicular traffic including cars and trucks on a roadway, said housing is on the center of said roadway, at least one camera is facing upwards toward said underbody, and control leads and cables extend from said housing to said control station and display remotely located from said roadway.

9. The system of claim 2 wherein said moving vehicle is a water borne marine vessel on water, said housing is located in a marine passageway in water beneath said underbody of said marine vessel, at least one camera is facing upwards toward said underbody, and control leads and cables extend from said housing to said control station and screen remotely located from said marine passageway.

10. The system of claim 7 wherein said moving vehicle is an aircraft on a taxiway, said housing is on said taxiway, at least one camera is facing upwards toward said underbody, and control leads and cables extend from said housing to said control station and screen located away from said taxiway.

11. The system of claim 2 wherein said radiation source radiates visible light and said video camera is responsive to visible light to produce said image signals.

12. The system of claim 2 wherein said radiation source radiates imperceptible radiation and said video camera is responsive to said imperceptible radiation to produce said image signals.

13. The system of claim 3 wherein said radiation source radiates visible light and said video camera is responsive to visible light to produce said image signals.

14. The system of claim 3 wherein said radiation source radiates imperceptible radiation and said video camera is responsive to said imperceptible radiation to produce said image signals.

15. The system of claim 4 wherein said radiation source radiates visible light and said video camera is responsive to visible light to produce said image signals.

16. The system of claim 4 wherein said radiation source radiates imperceptible radiation and said video camera is responsive to said imperceptible radiation to produce said image signals.

17. A method of imaging the underbody of a moving vehicle comprising the steps of:
 radiating energy upwardly on an underbody of a moving vehicle, said step of radiating includes the step of:
 placing a stationary source of radiation to radiate upwardly;
 creating image signals representative of sequential portions of said moving vehicle's underbody passing overhead said step of creating image signals includes the step of:
 facing upwardly a stationary video camera having a field of view extending the width of said vehicle passing overhead, said stationary video camera being adjacent said radiation source;
 activating said radiation source and video camera to create said image signals;
 creating mosaic signals of all of said underbody from said image signals from said video camera;
 displaying a mosaic image of said underbody from said mosaic signals;
 storing a copy of said mosaic signals, said steps of activating said radiation source and camera, creating mosaic signals and storing said copy being done by a computer coupled to said radiation source and said camera and said step of displaying being on a graphic display screen;
 storing in said computer earlier mosaic signals of previously taken mosaic images of the underbody of the same vehicle and vehicle manufacturers' data for the same vehicular model;
 comparing in said computer said copy of said mosaic signals and said earlier mosaic signals; and
 protecting said stationary camera and said radiation source from said moving vehicle in elongate channels between ridges extending the length of an elongate housing placed on the center portion of a roadway between the areas where tires of vehicles normally roll, said housing having an elongate hinged protective lid to cover said channels and ridges.

18. The method of claim 17 further comprising the step of:
 providing a field of view for said stationary camera to extend the width of said moving vehicle thereby assuring that said image signals are representative of said sequential portions of said underbody extending said width.

19. The method of claim 18 further comprising the step of:
 installing a plurality of cameras in said channels to create collective sequential image signals that collectively span the entire width and said sequential portions of said moving vehicle, said computer creating said mosaic signals from collective image signals.

20. The method of claim 19 further comprising the steps of:
 facing one of said cameras toward approaching traffic to create frontal image signals of said moving vehicle and another of said cameras toward departing traffic to create rear image signals of said moving vehicle.

21. The method of claim 20 further comprising the step of:
 identifying said moving vehicle from said frontal image signals and said rear image signals in said computer.

22. The method of claim 21 further comprising the step of:
 rotating a hinged lid of said housing to selectively uncover said channels to expose said cameras and radiation source and to selectively cover said channels with said hinged lid and abut said ridges to protect said cameras and radiation source from moving vehicles.

23. The method of 22 wherein said moving vehicle is part of motor vehicular traffic including cars and trucks on a roadway, said housing is on the center of said roadway with at least one camera facing upwards toward said underbody and control leads and cables extend from said housing to said computer and display screen remotely located from said roadway.

24. The method of claim 22 wherein said moving vehicle is a water borne marine vessel on water, said housing is located in a marine passageway in water beneath said underbody of said marine vessel, at least one camera is facing upwards toward said underbody, and control leads and cables extend from said housing to said computer and display screen remotely located from said lane.

25. The method of claim 22 wherein said moving vehicle is an aircraft on a taxiway, said housing is on the center of said taxiway, at least one camera is facing upwards toward said underbody, and control leads and cables extend from said housing to said computer and display screen located away from said taxiway.

26. The method of claim 18 wherein said step of radiating includes the step of:
 illuminating said underbody with visible light from said radiation source and said video camera is responsive to visible light to produce said image signals.

27. The method of claim 18 wherein said step of radiating includes the step of:
 illuminating said underbody with imperceptible radiation and said video camera is responsive to said imperceptible radiation to produce said image signals.

28. The method of claim 19 wherein said step of radiating includes the step of:
 illuminating said underbody with visible light from said radiation source and said video camera is responsive to visible light to produce said image signals.

29. The method of claim 19 wherein said step of radiating includes the step of:
 illuminating said underbody with imperceptible radiation and said video camera is responsive to said imperceptible radiation to produce said image signals.

30. The method of claim 20 wherein said step of radiating includes the step of:
 illuminating said underbody with visible light from said radiation source and said video camera is responsive to visible light to produce said image signals.

31. The method of claim 20 wherein said step of radiating includes the step of:
 illuminating said underbody with imperceptible radiation and said video camera is responsive to said imperceptible radiation to produce said image signals.

* * * * *